US00PP12565P2

(12) United States Plant Patent
Vandenberg et al.

(10) Patent No.: US PP12,565 P2
(45) Date of Patent: Apr. 23, 2002

(54) CHRYSANTHEMUM PLANT NAMED 'YOGISELE'

(75) Inventors: Cornelis P. Vandenberg, Salinas, CA (US); Wendy R. Bergman, Lehigh Acres, FL (US)

(73) Assignee: Yoder Brothers, Inc., Barberton, OH (US)

( * ) Notice: Subject to any disclaimer, the term of this patent is extended or adjusted under 35 U.S.C. 154(b) by 0 days.

(21) Appl. No.: 09/774,361

(22) Filed: Feb. 1, 2001

(51) Int. Cl.[7] ..... A01H 5/00
(52) U.S. Cl. ..... Plt./298

(58) Field of Search ..... Plt./298

*Primary Examiner*—Bruce R. Campell
*Assistant Examiner*—Anne Marie Grünberg
(74) *Attorney, Agent, or Firm*—C. A. Whealy

(57) ABSTRACT

A distinct cultiver of Chrysanthemum plant named 'Yogisele', characterized by its upright and uniformly rounded plant habit; dark green foliage; very freely branching habit, full and dense plants; uniform flowering response; early flowering, eight-week response time; very freely flowering habit; small daisy-type inflorescences that are about 3.6 cm in diameter; red ray florets and bright yellow disc florets; and excellent postproduction longevity with plants maintaining good substance and color for about three to four weeks in an interior environment.

1 Drawing Sheet

BACKGROUND OF THE INVENTION

The present Invention relates to a new and distinct cultivar of Chrysanthemum plant, botanically known as *Chrysanthemum×morifolium* and hereinafter referred to by the name 'Yogisele'.

The new Chrysanthemum is a product of a planned breeding program conducted by the Inventors in Salinas, Calif. The objective of the breeding program is to create new potted Chrysanthemum cultivars that are suitable for year-round production with uniform plant growth habit, desirable inflorescence form and floret colors, fast response time, and excellent postproduction longevity.

The new Chrysanthemum originated from a cross made by the Inventors in October, 1994, in Salinas, Calif., of a proprietary Chrysanthemum seedling selection identified as code number YB-6364, not patented, as the female, or seed, parent with a proprietary Chrysanthemum seedling selection identified as code number YB-6075, not patented, as the male, or pollen, parent. The new Chrysanthemum was discovered and selected by the Inventors as a single flowering plant within the progeny of the stated cross grown in a controlled environment in Salinas, Calif. The selection of this plant was based on its uniform plant growth habit, desirable inflorescence form and floret colors, fast response time, and excellent postproduction longevity. Plants of the new Chrysanthemum differ primarily from plants of the parent selections in ray floret coloration.

Asexual reproduction of the new Chrysanthemum by vegetative tip cuttings was first conducted in Fort Myers, Fla. in June, 1997. Asexual reproduction by cuttings has shown that the unique features of this new Chrysanthemum are stable and reproduced true to type in successive generations.

SUMMARY OF THE INVENTION

The cultivar Yogisele has not been observed under all possible environmental conditions. The phenotype may vary somewhat with variations in environment such as temperature, daylength, and/or light level, without, however, any variance in genotype.

The following traits have been repeatedly observed and are determined to be the unique characteristics of 'Yogisele'. These characteristics in combination distinguish 'Yogisele' as a new and distinct Chrysanthemum:

1. Upright and uniformly rounded plant habit.
2. Very freely branching habit, full and dense plants.
3. Dark green foliage.
4. Uniform flowering response.
5. Typically grown as a natural spray-type.
6. Early flowering, eight-week response time.
7. Very freely flowering.
8. Small daisy-type inflorescences that are about 3.6 cm in diameter.
9. Red ray florets and bright yellow disc florets.
10. Excellent postproduction longevity with plants maintaining good substance and color for about three to four weeks in an interior environment.

Plants of the new Chrysanthemum can be compared to plants of the Chrysanthemum cultivar Bronze Cherie, disclosed in U.S. Plant Pat. No. 9,702. In side-by-side comparisons conducted by the Inventors in Salinas, Calif., plants of the new Chrysanthemum differ from plants of the cultivar Bronze Cherie in the following characteristics:

1. Plants of the new Chrysanthemum are much larger and more vigorous than plants of the cultivar Bronze Cherie.

2. Plants of the new Chrysanthemum flower more uniformly than plants of the cultivar Bronze Cherie.

3. Plants of the new Chrysanthemum flower about 2 to 3 days earlier than plants of the cultivar Bronze Cherie 4. Plants of the new Chrysanthemum have larger inflorescences than plants of the cultivar Bronze Cherie.

5. Ray floret color of the new Chrysanthemum is red whereas ray floret color of the cultivar Bronze Cherie is bronze.

6. Inflorescences of the new Chrysanthemum do not produce pollen whereas inflorescences of the cultivar Bronze Cherie produce abundant pollen.

BRIEF DESCRIPTION OF THE PHOTOGRAPHS

The accompanying colored photographs illustrate the overall appearance of the new Chrysanthemum showing the colors as true as it is reasonably possible to obtain in colored reproductions of this type. Colors in the photographs may differ from the color values cited in the detailed botanical description which accurately describe the colors of the new Chrysanthemum.

The photograph at the top of the sheet comprises a top perspective view of a typical flowering plant of 'Yogisele' grown a natural spray-type.

The photograph at the bottom of the sheet comprises a close-up view of typical inflorescences of 'Yogisele' grown as a natural spray-type.

DETAILED BOTANICAL DESCRIPTION

In the following description, color references are made to The Royal Horticultural Society Colour Chart except where general terms of ordinary dictionary significance are used. The following observations and measurements describe plants grown and flowered during the autumn in Salinas, Calif., in a fiberglass-covered greenhouse and under conditions which approximate those generally used in commercial potted Chrysanthemum production. During the production of these plants, the following conditions were measured: day temperatures, 21 to 27° C.; night temperatures, 17 to 19° C.; and light levels, 5,000 to 6,000 foot-candles. Four unrooted cuttings were directly stuck in 15-cm containers, exposed to long day/short night conditions, and pinched once about 14 days later. At that time, the photoinductive short day/long night treatments were started. Plants used for this description were grown as natural spray-types. Measurements and numerical values represent averages of typical flowering plants.

Botanical classification: *Chrysanthemum×morifolium* cultivar Yogisele.

Commercial classification: Daisy-type potted Chrysanthemum.

Parentage:

*Female, or seed, parent.*—Proprietary *Chrysanthemum×morifolium* seedling selection identified as code number YB-6364, not patented.

*Male, or pollen, parent.*—Proprietary *Chrysanthemum×morifolium* seedling selection identified as code number YB-6075, not patented.

Propagation:

*Type.*—Terminal tip cuttings.

*Time to initiate roots.*—About four days at 21° C.

*Time to produce a rooted cutting.*—About ten days at 21° C.

*Root description.*—Fibrous and well-branched.

Plant description:

*Appearance.*—Herbaceous daisy-type potted Chrysanthemum typically grown as a natural spray-type. Stems mostly upright and outwardly spreading giving a uniformly rounded appearance to the plant. Very freely branching, about five to six lateral branches develop after removal of terminal apex (pinching); dense and full plants. Moderate vigor.

*Plant height.*—About 29 cm.

*Plant width.*—About 46 cm.

*Lateral branches.*—Length: About 26 cm. Diameter: About 4 mm. Internode length: About 1.8 cm. Strength: Strong; flexible. Texture: Pubescent. Color: Slightly darker than 144A.

*Foliage description.*—Arrangement: Alternate. Quantity of leaves per lateral stem: About 14. Length: About 5.8 cm. Width: About 3.9 cm. Apex: Cuspidate to mucronate. Base: Attenuate. Margin: Palmately lobed, sinuses between lateral lobes mostly divergent. Texture: Upper and lower surfaces with very fine pubescence; veins prominent on lower surface. Color: Young foliage, upper surface: Darker than 147A. Young foliage, lower surface: Darker than 147B. Mature foliage; upper surface: Darker than 147A. Mature foliage; lower surface: Close to 147B. Venation, both surfaces: Close to 146C. Petiole length: About 2.2 cm. Petiole diameter: About 3 mm. Petiole color: Close to 146C.

Inflorescence description:

*Appearance.*—Daisy-type inflorescence form with elongated oblong-shaped ray florets. Inflorescences borne on terminals above foliage. Disk and ray florets arranged acropetally on a capitulum. Not fragrant. Typically grown as a natural spray-type.

*Flowering response.*—Under natural conditions, plants flower in the autumn/winter in the Northern Hemisphere. At other times of the year, inflorescence initiation and development can be induced under short day/long night conditions (at least 13.5 hours of darkness). Early flowering; plants exposed to two weeks of long day/short night conditions followed by photoinductive short day/long night conditions flower about 48 days later when grown during the summer and flower about 56 days later when grown during the winter.

*Postproduction longevity.*—Inflorescences maintain good color and substance for about three to four weeks in an interior environment.

*Quantity of inflorescences.*—Very freely flowering, about 18 inflorescences develop per lateral stem, or about 90 to 108 inflorescences per plant.

*Inflorescence bud.*—Height: About 5 mm. Diameter: About 6.5 mm. Color: 143A.

*Inflorescence size.*—Diameter: Small, about 3.6 cm. Depth (height): About 1 cm. Diameter of disc: About 1.1 cm. Receptacle diameter: About 4.5 mm.

*Ray florets.*—Shape: Elongated-oblong. Orientation: Initially upright, then about 90° from vertical or perpendicular to peduncle. Aspect: Mostly flat. Length: About 1.7 cm. Width: About 5.5 mm. Corolla tube length: About 3 mm. Apex: Rounded, acute, emarginate or dentate. Base: Attenuate; short corolla tube. Margin: Entire. Texture: Smooth, glabrous, velvety. Number of ray florets per inflorescence: About 32 arranged in one or two rows. Color: When opening, upper surface: Initially, 187A; then 9A overlain 53A to 185A; base, 9A. Overall tonality, close to 46A. When opening, lower surface: Initially, 187A; then 9B underlain with 53A to 185A. Fully opened, upper surface: 9A overlain with 53A to 185A; base, 9A. Overall tonality, close to 45A. Fully opened, lower surface: 9B to 9C underlain with 53A to 185A.

*Disc florets.*—Arrangement: Massed at center of receptacle. Shape: Tubular, elongated. Apex: Fivepointed. Length: About 6 mm. Width: Apex, about 1.5 mm; base, about 1 mm. Number of disc florets per inflorescence: About 109. Color: Immature: 154A. Mature: Apex: 9A. Mid-section: 145A. Base: 155D.

*Peduncles.*—Length: First peduncle: About 4.5 cm. Fourth peduncle: About 7.9 cm. Seventh peduncle: About 10.6 cm. Diameter: About 2 mm. Angle to vertical: About 40 to 45° from vertical. Strength: Strong, flexible. Color: 144A.

*Reproductive organs.*—Androecium: Present on disc florets only. Anther color: 9A to 12A. Pollen amount: None. Gynoecium: Present on both ray and disc florets.

*Seed.*—Seed production has not been observed.

Disease resistance: Resistance to pathogens common to Chrysanthemums has not been observed on plants grown under commercial greenhouse conditions.

It is claimed:

1. A new and distinct cultivar of Chrysanthemum plant named 'Yogisele', as illustrated and described.

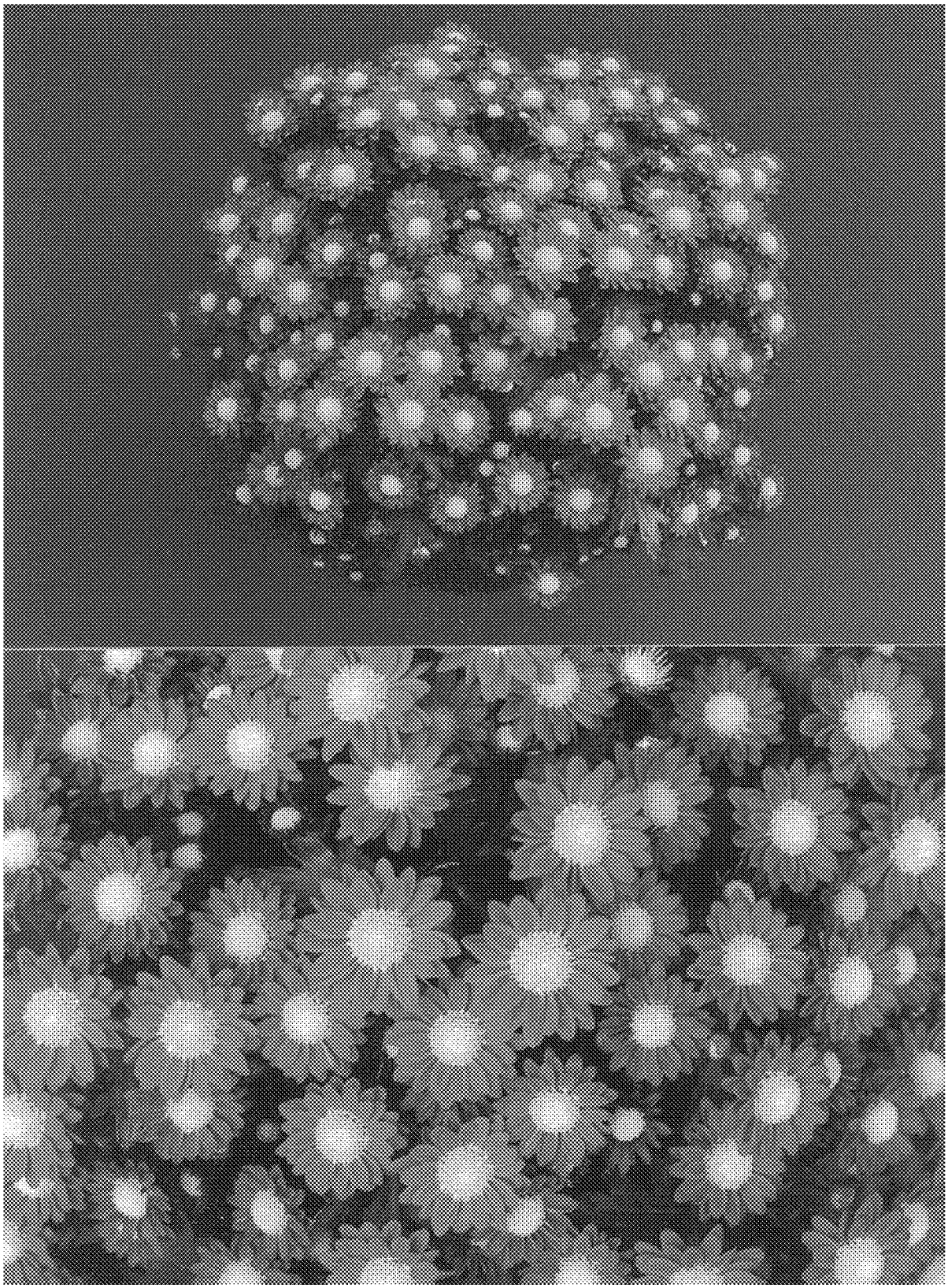

* * * * *